United States Patent [19]
D'Alessio et al.

[11] Patent Number: 5,913,850
[45] Date of Patent: *Jun. 22, 1999

[54] ABSORBENT ARTICLE

[75] Inventors: Nicola D'Alessio, Pescara; Giovanni Carlucci, Chieti, both of Italy

[73] Assignee: The Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 08/849,608

[22] PCT Filed: Nov. 21, 1995

[86] PCT No.: PCT/US95/15190

§ 371 Date: Jun. 2, 1997

§ 102(e) Date: Jun. 2, 1997

[87] PCT Pub. No.: WO96/16622

PCT Pub. Date: Jun. 6, 1996

[30] Foreign Application Priority Data

Dec. 1, 1994 [IT] Italy ................ T094A0982

[51] Int. Cl.⁶ .................................. A61F 13/15
[52] U.S. Cl. ............................ 604/378; 604/370
[58] Field of Search ................... 604/358, 378, 604/370

[56] References Cited

U.S. PATENT DOCUMENTS

| | | |
|---|---|---|
| 5,387,208 | 2/1995 | Ashton et al. ............. 604/378 |
| 5,462,537 | 10/1995 | Carr et al. . |
| 5,482,761 | 1/1996 | Palumbo et al. . |
| 5,549,589 | 8/1996 | Horney et al. . |
| 5,591,149 | 1/1997 | Cree et al. . |
| 5,603,707 | 2/1997 | Trombetta et al. . |
| 5,628,736 | 5/1997 | Thompson . |
| 5,681,300 | 10/1997 | Ahr et al. . |
| 5,704,101 | 1/1998 | Majors et al. . |
| 5,728,084 | 3/1998 | Palumbo et al. . |
| 5,762,641 | 6/1998 | Bewick-Sonntag et al. . |

FOREIGN PATENT DOCUMENTS

| | | |
|---|---|---|
| WO 94/06385 | 3/1994 | WIPO . |
| WO 94/28838 | 12/1994 | WIPO . |
| WO 95/17868 | 7/1995 | WIPO . |
| WO 95/24878 | 9/1995 | WIPO . |
| WO 97/17923 | 5/1997 | WIPO . |

Primary Examiner—John G. Weiss
Assistant Examiner—Dennis Ruhl
Attorney, Agent, or Firm—Theodore P. Cummings; Steven W. Miller; Jacobus C. Rasser

[57] ABSTRACT

An article is described for absorbing body fluid from a wearer. This comprises a fluid storage region (7) having a first major face on one side thereof and a second major face on the opposite side thereof, and first (6) and second (8) fluid receiving regions adjacent the first and second major faces respectively. Each fluid receiving region (6, 8) receives fluid and releases it to the adjacent major face of fluid storage region. The fluid receiving regions (6, 8) are each formed of a dry laid web of staple fibers, the web having a bulkiness, as measured under a pressure of 2 kPa, of at least 20 cc/g.

43 Claims, 3 Drawing Sheets

ABSORBENT ARTICLE

This invention relates to an absorbent article. It is particularly concerned with an absorbent article, for example in the form of a pad, which can be used by women suffering from light and moderate incontinence. The invention will be so described below. However, the invention is of more general applicability in relation to the absorption of body fluids, either urine or menstrua. It can therefore be used, for example, in the manufacture of infant diapers, and in incontinence products for adults, in addition to the incontinence product specifically identified above.

A condition of light incontinence exists in many women. An absorbent pad, or other article, for use by those with this condition should desirably (a) Be thin, and with a shape fitting well into the underpants, to provide discretion when worn under normal clothing.

(b) Be absorbent enough to handle large quantities of urine.

(c) Absorb rapidly enough to accept the surge of urine (gush handling) that can occur from women who have this condition, and maintain this capability even through multiple gushes.

Research indicates that 10–20% of the female population suffer from light involuntary urine losses. The magnitude of the problem varies from losing just a few dribbles in special situations (coughing, sneezing, during sports) to a more serious, permanent problem (after menopause or in conjunction with gynaecological operations). The product selected by such women, and the usage frequency, depends on the seriousness of the problem: pantiliner usage with 1–2 changes per day for occasional urine losses moving to a higher change frequency (2–8 pantiliners/day) for higher loadings and/or more frequent bladder weakness. For those at the upper end of the problem range, pantiliners are not sufficiently absorbent, besides being prone to bunching and to disintegration during use, and such women use 2–3 catamenial pads per day.

Existing products for light incontinence are similar to oversized thick catamenial pads. Most are very thick, about 15 mm thick, and this does not provide the degree of discretion the user desires. Furthermore, these products have absorbent cores that typically collapse when wetted, thus making them deficient in fluid absorption rate for subsequent loadings.

For the lightest conditions of light incontinence, many women use standard pantiliners. These products provide the desired level of discretion under clothing; however, they are totally inadequate in absorbency. Part of this deficiency is in absorbent capacity, but more important is the deficiency in absorbent rate.

One object of the present invention is to provide an absorbent article for dealing with light and moderate incontinence, which is discrete, has the absorbent capacity required, and has the necessary gush handling ability.

Our International Patent Application No. PCT/EP94/01814 provides, in one aspect thereof, an article for absorbing fluid, which comprises a fluid-storage region and a fluid-receiving region adapted to release fluid to the fluid-storage region, the fluid-receiving region being formed of a dry laid, for example an airlaid, web of staple fibers, the web having a bulkiness, as measured under a pressure of 2 kPa, of at least 15 cm$^3$/g, preferably at least 20 cm$^3$/g. The article described there preferably further comprises a water-permeable topsheet in face-to-face relationship with the said fluid-receiving sheet, on the opposite side thereof to the fluid-storage sheet, and a water-impermeable backsheet in face-to-face relationship with the fluid-storage sheet, on the opposite side thereof to the fluid-receiving sheet. The topsheet and backsheet are preferably sealed to one another, and the article shaped to form a pad suitable for incontinent females.

By "staple fibers" we mean fibers which are not continuous, and which may be synthetic fibers, natural fibers, or a mixture of synthetic and natural fibers.

It is believed that the high bulkiness of the fluid-receiving region is such that the fluid is free to flow with very little impedance by the fibers defining the region. This is in contrast to the approach adopted in known products dealing with incontinence, where any fluid-receiving region serves as a wick to transfer fluid received at one part of the region to other parts thereof. However, it is to be understood that this explanation is offered here as a suggestion only, and no categorical assertion is made that it is correct.

An object of an aspect of the present invention is to provide advantageous developments of the article of the type described in the above International Patent Application. In one form thereof, the present application provides an article for absorbing body fluid from a wearer, which comprises a fluid-storage region having a first major face on one side thereof and a second major face on the opposite side thereof, and first and second fluid-receiving regions adjacent the said first and second major faces respectively, each fluid-receiving region being adapted to receive fluid and release it to the adjacent major face of the fluid-storage region, the fluid-receiving regions each being formed of a material which has a bulkiness, as measured under a pressure of 2 kPa, of at least 20 cm$^3$/g. Preferably the material is a dry laid web of staple fibers.

Despite the presence of fluid-receiving regions on both sides of the fluid-receiving region, the absorbent article can be thin, being as little as 3 mm in thickness, or even less, and provided it has the correct contours to fit well into underwear can be highly discreet. The key is that the article swells only when heavily wetted. This is in contrast to existing products on the market, which if they provide anything approaching an acceptable level of absorbence, are bulky even when dry.

The presence of a second fluid-receiving region, on the opposite side of the fluid-storage region (hereinafter referred to as "the core") to the first fluid-receiving region, increases the temporary storage capacity of the article, enabling a greater quantity of urine or other body liquid to be held until it can be absorbed by the core. The fact that these fluid-receiving regions exist on both sides of the core helps to ensure that the fluid is fed with maximum efficiency to the core. This is particularly important where the core comprises a polymeric hydrogel material (commonly referred to as an AGM material). Such materials are subject to what is known as gel-blocking, where absorption of liquid by one region of the AGM prevents or hinders fluid reaching the remainder of the AGM. Having fluid-receiving regions on both sides of the AGM-containing core means that fluid is efficiently distributed to, and absorbed by, both sides of the core.

Also, having the two fluid-receiving regions, with the core sandwiched between, means that the core is to some extent cushioned against compressive forces which may be applied to the article, thus reducing the possibility of fluid being squeezed out of it. Furthermore, in so far as such squeezing does take place, the fluid which emerges from the core is taken up substantially immediately by the fluid-receiving regions. The fact that, according to this aspect of the invention, such a region is provided on the side of the core nearer the backsheet, as well as on the other side thereof, is particular advantageous, since to the extent that the fluid emerges on one side of the core rather than the other it will be on the lower side, i.e. the backsheet side, as a result of the effect of gravity.

According to another aspect of the present invention there is provided an article for absorbing body fluid from a wearer's body, which comprises at least three layers of material adapted to receive and/or store said body fluid, the article being elongate and having a major axis running along its length and a minor axis running along its width, wherein the sheet nearest that face thereof which is intended to be adjacent a wearer's body has a width less than the sheet adjacent that opposite face which is intended to face away from the wearer's body, and wherein each sheet is at least as wide as the adjacent sheet, if any, nearer the wearer's body and is not wider than the adjacent sheet, if any further away from the wearer's body. This aspect is referred to below, for convenience, as the "pyramid" feature.

In one preferred form of the invention the absorbent article to which the pyramid aspect is applied is an article of the type to which International Patent Application No. PCT/EP94/01814 relates. Still more preferably it is applied to an article as defined above in relation to the first aspect of this invention, i.e. one in which there are fluid-receiving regions on both sides of the core.

Where the pyramid feature is applied to an article having more than three layers, it is to be understood that although the width may increase from each layer to the next, it is also possible for two adjacent layers to have the same width. The pyramid feature gives the article a better fit to the wearer, and hence makes it more comfortable to wear.

Figure 1:
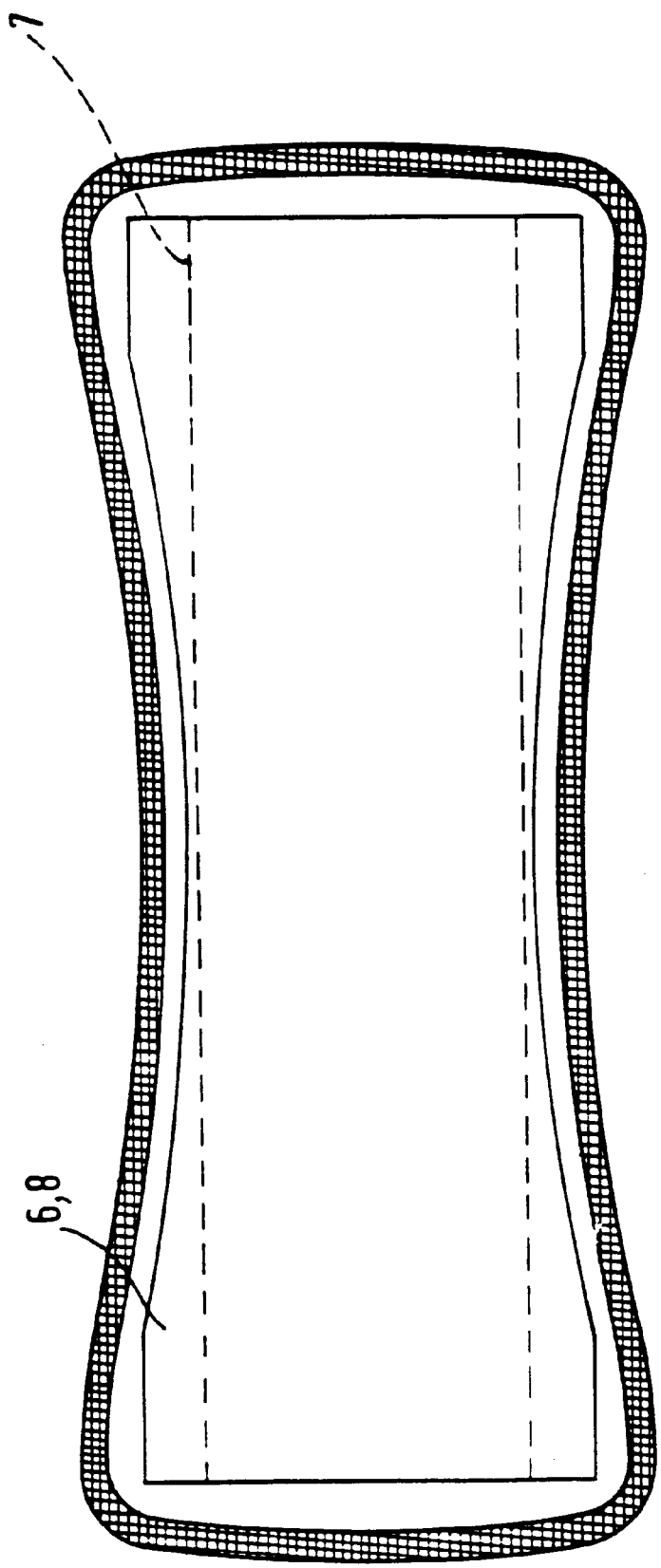
FIG. 1 is a plan view of a first embodiment of an absorbent article according to the present invention.
Figure 2:
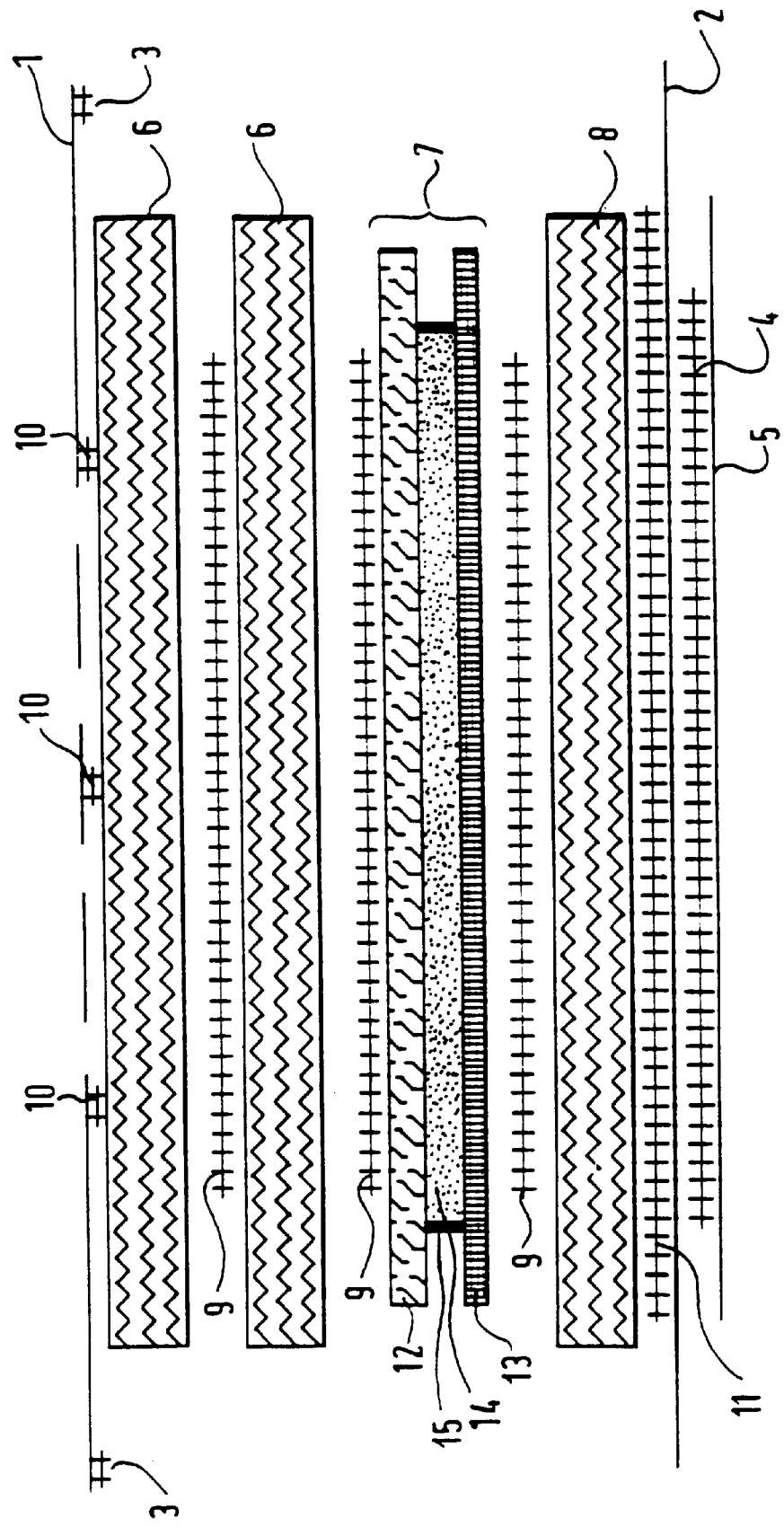
FIG. 2 is a diagrammatic cross-section, on a larger scale, through the crotch region of the article shown in FIG. 1.

The embodiment of FIGS. 1 and 2 comprises a liquid permeable topsheet 1 and a liquid impermeable backsheet 2 sealed to one another along a peripheral region 3 thereof by, for example, thermal bonding. The backsheet 2 has a layer 4 of hot-melt adhesive coated thereon, to which is attached a release sheet 5 which is removed by the user before use. Within the enclosure defined by the topsheet 1 and backsheet 2 there are provided an absorbent storage core 7, two secondary topsheets 6 located between the core 7 and the topsheet 1, and a secondary bottom sheet 8 located between the core 7 and the backsheet 2. The sheets 6, core 7 and sheet 8 are attached to one another by layers 9 of cold glue. The layers 9 are discontinuous, so that liquid can pass therethrough. Depending on the capacity required, it may be sufficient to have only one secondary topsheet 6.

The layers 9 are preferably of the type disclosed in our copending International Patent Application No. PCT/EP94/01576 filed on 16th May 1994 and entitled "Adhesive composition". The International Application describes a water-based adhesive composition comprising a blend of adhesive polymers in an aqueous system, characterised in that the blend of adhesive polymers is:

20–60% by weight of an acrylic polymer having a polarity balance expressed as water absorption according to DIN 53495 of 3 to 20%; and correspondingly 40–80% by weight of a compatible tackifying resin having a degree of hydrophobicity measured as the contact angle between a dried film of the resin and a drop of distilled water of not less than 60°;

the percentages being based on the total of acrylic polymer plus tackifying resin expressed as dry solids.

The upper one of the sheets 6 is attached to the topsheet 1 by a plurality of narrow stripes 10 of hot-melt adhesive. The secondary bottom sheet 8 is attached to the backsheet 2 by a layer 11 of hot melt adhesive.

It can be seen that the core 7 consists of three layers, namely upper and lower layers 12 and 13 each of a cellulose-based material, and a middle layer 14 of a water-insoluble hydrogel material (AGM). At the edges of the layer 14 are lines of adhesive 15 which serve to confine the AGM material and prevent liquid therein leaking out.

The absorbent article will now be described in more detail with reference to the four layers thereof.

1. Topsheet

The top layer (user side) is a topsheet that must be comfortable to the touch, provide a dry feeling over an absorbent core filled with liquid, and pass fluid rapidly into the interior of the core. It is liquid permeable in the central longitudinal zone and is liquid impermeable at least in the two lateral zones in order to handle totally the urine during the gush, while avoiding lateral leakage. The width of the liquid impermeable area is such that even when the article is wet to its maximum extent, and is correspondingly swollen, the fluid permeable area of the sheet is not in communication with the lateral edges of the fluid-receiving secondary sheet. This avoid lateral leakage from the core. The liquid impermeable area may extend completely around the liquid permeable area.

This element can be of a variety of known materials, for example: a) a formed-film topsheet as described in U.S. Pat. No. 3,929,135, or any of European Patent specifications Nos. EP-A-0018020, EP-A-0018684 and EP-A-0059506 (b) a partially perforated fiber/film composite described in EP-A-207904, the perforated area thereof providing a liquid permeable area, and the unperforated area thereof providing a liquid impermeable area, or (c) a nonwoven film produced by the spunbonding or by a carded, thermal-bonded process, or a sheet produced by various other processes currently practised.

2. Secondary topsheets and secondary bottom sheet

Each of these elements has the characteristics of accepting a high rate of fluid intake, serving as a temporary reservoir for the fluid, and then draining substantially completely into the storage core (or, in the case of the upper secondary topsheet, into the lower secondary topsheet) in order to remain empty for subsequent fluid loadings. In addition, these elements must resist collapse when wet so that they maintain their performance through multiple loadings. The elements must do all these things while also remaining extremely thin. An airlaid web of synthetic fibres can be used for this purpose, the fibres being of a material which is inherently hydrophobic but has been rendered hydrophilic.

The use of fibers which are of a material which is inherently hydrophobic, but is rendered permanently hydrophilic means that the web allows fluid to enter it but also releases the fluid readily to the core, an effect in which the high bulkiness also plays a significant role.

Each of the elements preferably has the same bulkiness, and is preferably made of the same fibers, though the elements may have different thicknesses, and hence different basis weights.

The secondary sheet preferably has the following characteristics:

(a) A thickness of from 1 to 10 mm, more preferably from 1.5 to 6 mm, still more preferably from 1.7 to 4.5 mm, and even more preferably from 2 to 4 mm, the thickness being measured with the sheet under a pressure of 2 kPa.

(b) A basis weight of from 25 to 300 g/m², more preferably from in excess of 40 up to 40 to 200 g/m², still more preferably from 42 or 43 to 200 g/m², and yet more preferably from 50 to 180 g/m². Typically, it may be up to 150 cm³/g. For example, basis weights of 45, 60, 80 and 120 g/m² have been used and found to be satisfactory.

(c) As already mentioned, the sheet has a bulkiness of at least 20 cm³/g, when the sheet is under a pressure of 2 kPa. More preferably, the bulkiness is from 20 to 65 cm³/g, still more preferably from 20 to 60 cm³/g, and yet more preferably from 25 to 55 cm³/g. It may advantageously be from 30 to 50 cm³/g. Desirably, the minimum value for the bulkiness is 32, 33, 34 or 35 cm³/g.

(d) The ability to discharge to the storage core at least 95%, and more preferably at least 99% of the fluid which it receives in a loading.

(e) A wet collapse at 2.7 kPa of not more than 45%, and more preferably not more than 40%.

(f) A wet resilience at 0.1 kPa of not more than 40%, more preferably not more than 30%, and still more preferably not more than 25%.

(g) A wetting time of not more than 5 seconds, and preferably not more than 2 seconds.

(h) It is formed of fibres having a diameter of not more than 40 $\mu$m, preferably not more than 20 $\mu$m, and still more preferably from 15–20 $\mu$m, and a length of not more than 20 mm, preferably not more than 12 mm, and most preferably about 6 mm.

3. Storage Core

The third layer is a thin, high-capacity absorbent core. While thin when dry, this element of the structure preferably expands when wetted to provide a high, tenacious fluid-holding ability, and it must avoid collapse when wet. The storage core is itself preferably formed of a plurality of layers. For example, a three layer structure may be used in which the outer layers are of a cellulose tissue material (and may be the same as, or different from, one another). The middle layer is of a water-insoluble hydrogel (AGM), which is a polymeric material in particulate form, capable of absorbing a large quantity of liquid and retaining it under moderate pressures.

It is important that the secondary topsheets and secondary bottom sheet (hereinafter referred to generically as "secondary sheets") and the storage core work together. In particular, given the form of secondary sheet used herein, it is possible in this structure to avoid the typical problem of gel blocking in the storage core, because the secondary sheets provide total distribution of the fluid, and then drain it, directly or indirectly, into the storage core, from both major faces thereof, whenever the storage core is not saturated.

As an alternative to the form of storage core described above, it can be one of a number of thin, high-capacity materials. For example, the storage core can be a sheet of fused AGM particles as described in International Patent Publications Nos. WO91/14733, WO91/14734, WO91/15362 and WO91/15368 or a high capacity foam, as described, for example, in International Patent Publications Nos. WO93/04092, WO93/03699, WO93/04093, WO93/04113 and WO93/04115.

4. Impervious backsheet

The backsheet is impervious to liquids and, thus, prevents fluid which may be expressed from absorbent core from soiling the body or clothing of the user. Suitable materials are well known in the art, including woven and nonwoven fabrics which have been treated to render them liquid repellent. Breathable or vapour previous, liquid resistant materials, and those materials described in U.S. Pat. No. 3,881,489 and U.S. Pat. No. 3,989,867 can also be used. Preferred materials are those materials that are fluid and vapour impervious, because they provide additional fluid strikethrough protection. Especially preferred materials include formed thermoplastic films.

EXAMPLE 1

The topsheet is a partially perforated fiber/film composite coverstock of the type described in EP-A-0207904. It is partially perforated over a rectangular area which runs lengthwise and centrally of the pad and which has a width of 38 mm.

The secondary sheets are all formed using a hydrophilic resin from Dow Chemical called ASPUN (CODE XU 61518.11) which is a polyethylene resin containing a wetting agent, of the type described in U.S. Pat. No. 4,578,414. Polyethylene itself is inherently hydrophobic. Bicomponent crimped fibers are formed incorporating this wettable resin internally. The fibers comprise a polypropylene portion and a portion which is formed of the wettable resin mixed with LLDPE (linear, low density polyethylene). At least the latter portion has at least part of its surface exposed to the exterior of the fiber. The fibers are thus rendered permanently hydrophilic. The fibers will normally have a spin finishing agent on their surface. This is provided in order to assist in the spinning process, but it has the incidental effect of rendering the fibers temporarily hydrophilic. However, the spin finishing agent is largely washed off by the first gush of fluid. The wetting agent referred to above, by contrast, makes the fibers permanently hydrophilic.

The fibers are cut into staple fibers 6 mm in length, and the staple fibers are airlaid to form a resilient web of wholly synthetic, hydrophilic fibers. The fibers have a diameter of about 18 $\mu$m. The process of airlaying includes the step of applying heat or an adhesive to cause those fibers which touch, or almost touch, one another to bond to each other and those points. Preferably, at least the major part of the fibers of the secondary sheet are the bicomponent fibers, and more preferably substantially 100% are, and most preferably 100% are.

The properties of the secondary sheet thus formed, using 100% bicomponent fibers, and using thermal bonding, are given in the following table under the heading Element 2. By way of comparison, the second column gives the properties of a secondary sheet used in an existing product sold for light incontinence by Kimberly Clark Corporation under the name Poise Pads R.A. For the purpose of the comparison test, a secondary sheet was removed from a Poise pad.

|  | Element 2 | Poise Pad R.A. 2nd Sheet |
|---|---|---|
| Basis Weight (g/m²) | 60 | 130 |
| Caliper (mm @ 2 kPa pressure) | 2.3 | 1.6 |
| Bulkiness (cc/g) @ 2 kPa pressure) | 38.3 | 12.3 |
| Dunk capacity (g/g/ @ P = 0) | 36.5 | 20.6 |
| Fluid Retention (g/g) | 0.01 | 1.5 |
| Fluid % discharge* | 99.97 | 92.72 |
| Wet Collapse (% loss @ 2.7 kPa) | 37.1 | 48.7 |
| Wet Resilience (% loss @ 0.1 kPa) | 17.7 | 42.5 |
| Wetting Time (sec) | 0.2 | 7.2 |

*Fluid % discharge = (Dunk capacity - Fluid Retention) /Dunk capacity × 100.

The table above demonstrates the superiority of the secondary sheet used in the invention in each of a number of important performance areas.

The high bulkiness demonstrates that it has a high void volume, and has the ability to acquire fluid efficiently.

The wetting time demonstrates the wettability of the web.

The low fluid retention value demonstrates the ability of the secondary sheet to drain the fluid almost completely (give up fluid into the storage core or other secondary sheet beneath it), so that the secondary sheet drains completely and is therefore available for subsequent loadings.

The low wet collapse and low wet resilience values show that neither the capillary forces of fluid inside the structure, nor external pressure loadings, cause a harmful loss of the open void volume required for the structure to perform well.

The dunk capacity describes the property of being filled substantially totally with urine.

The storage core is a three-layer structure laminate, having the following layers:

a) A top layer having a weight of 75 g/m$^2$, of dry-formed, thermal-bonded, cellulose tissue with bicomponent polyolefin staple fibers. The latter are polyethylene-polypropylene ES-C fibers from Danaklon A/S, with a denier of 1.7 dtex and a length of 6 mm, the fibers consisting of polypropylene with a polyethylene sheath.

b) Middle layer of particulate (100–800 micron) polyacrylate AGM Dow XZ type (200 g/m$^2$);

c) Bottom layer of air-laid, latex-bonded cellulose embossed tissue (55 g/m$^2$).

Alternatively, the structure may be made according to our Italian Patent Application No. TO 93A 001028, which has similarities to what is described in International Patent Publication No. WO94/01069, but which incorporates an AGM material in a higher basis weight.

The backsheet is a 25 μm coextruded polypropylene/polyethylene film.

Figure 3:
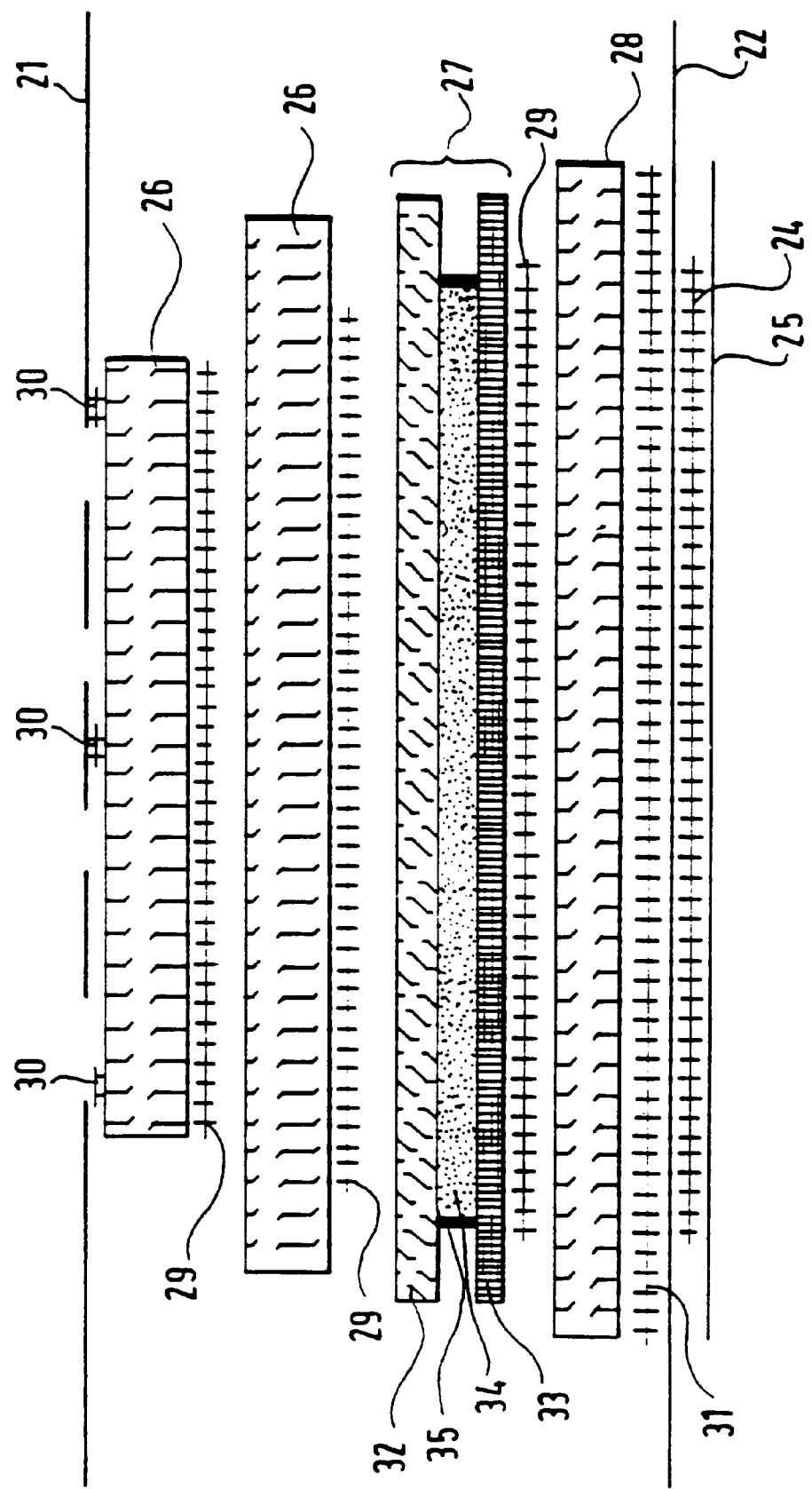
FIG. 3 is a view similar to FIG. 2, but showing a second embodiment of the invention.

Turning now to FIG. 3, this shows an embodiment which incorporates the pyramid feature referred to above. The reference numerals used in FIG. 3 corresponds to those used in FIGS. 1 and 2, but with the addition of 20. It will be seen there is a progressive increase in width as one goes from the upper secondary topsheet 26 to the lower secondary topsheet 26 to the core 27 to the secondary bottom sheet 28. FIG. 3 shows the pyramid arrangement as it exists in the crotch region. As in the case of FIGS. 1 and 2, the secondary topsheets and the secondary bottom sheet are each shaped to have a perimeter which runs approximately parallel to the edge of the article, but the core and both the secondary topsheets have straight side edges. Accordingly, the pyramid effect becomes greater as one moves away from the crotch region, because of the increasing width of the secondary bottom sheet.

It is to be understood that where, as in the case of FIG. 3, there are four layers of fluid-receiving or fluid-storing material, there will still be a pyramid if there are two adjacent layers which are of the same width. If there were more than four layers, a pyramid could still be obtained if there were more than two adjacent layers of the same width, or if there was more than the pair of layers of the same width. However, it is also possible for all layers to be greater in width than the layer above it.

In the embodiment shown in FIG. 3, the widths of the layers at the crotch are:

Upper secondary topsheet (26): 35 mm
Lower secondary topsheet (26): 42 mm
Core (27): 50 mm
Secondary bottom sheet (28): 54 mm The maximum width of the secondary bottom sheet is 72 mm. It is to be understood that all the dimensions are given by way of example only.

The following sets out the methods used to measure various parameters mentioned above:

Dunk capacity.

This method evaluates the free absorption capacity of the material. A rectangular sample of material 25.4×100 mm is put onto the surface of a liquid (synthetic urine, of which the composition is given below) and left on it for one minute. It is then withdrawn by means of a metallic net and left to drip in horizontal position for one minute.

The dunk capacity is obtained as:

(Wet weight–dry weight)/dry weight of the sample (g/g).

Fluid retention.

The samples obtained from the above test method are rotated in a centrifuge under a g-force of 240 g for ten minutes.

The fluid retention is obtained as:

(Wet weight–dry weight)/dry weight of the sample (g/g).

Wet collapse.

The samples 38×50 mm are made of as many superimposed layers of material as are needed to get an overall basis weight of 500 g/m$^2$. The samples are wetted in the same way as in the dunk capacity test. They are then placed on a perforated plexiglass plate and subjected to three dynamic cycles of compression and decompression (speed of the pressing head 10 mm/min, maximum load for each cycle 2.7 kPa). The minimum thickness of the sample under compression is measured.

The wet collapse is:

(initial thickness–minimum thickness/initial thickness of the sample)×100 (%).

Wet resilience.

In the above described test the final thickness of the sample after the last decompression is measured.

The wet resilience is then obtained as:

(initial thickness–final thickness)/(initial thickness)×100 (%).

Wetting time.

In this test, samples of the secondary sheet of the present invention and samples of the second sheet of Poise Pad R.A. having the same volume of about 5 cc are compared. The considered thicknesses correspond to the calipers under pressure (see the values on the table). The samples are placed horizontally onto the surface of water by means of a metallic net. The wetting time is the time needed for each sample to get completely soaked.

Composition of the synthetic urine used in the tests.

The synthetic urine is a solution in distilled water containing the following salts (in weight percent):

Urea 2%, sodium chloride 0.9%, magnesium sulphate (heptahydrate) 0.11%, calcium chloride 0.06%.

We claim:

1. An article for absorbing body fluid from a wearer, comprising a fluid-storage region having a first major face and a second major face opposed to said first major face, a first receiving region being held adjacent to said first major face of said fluid storage region and a second fluid-receiving region being held adjacent to said second major face, each said fluid-receiving region being adapted to receive fluid and release said fluid to said adjacent major face of said fluid-storage region, each said fluid-receiving region being formed of a material having a bulkiness, as measured under a pressure of 2 kPa, from about 20 cm$^3$/g to about 65 cm$^3$/g.

2. An article to claim, wherein the said bulkiness is not more than 65 cm$^3$/g.

3. An article according to claim 2, wherein the said bulkiness is not more than 60 cm$^3$/g.

4. An article according to claim 1, wherein said bulkiness is from about 25 cm³/g to about 55 cm³/g.

5. An article according to claim 4, wherein said bulkiness is from about 30 cm³/g to about 50 cm³/g.

6. An article according to claim 1, wherein said material of each said fluid-receiving region has a thickness ranging from about 1 mm to about 10 mm.

7. An article according to claim 6, wherein said thickness ranges from about 1.5 mm to about 6 mm.

8. An article according to claim 7, wherein said thickness is from about 1.7 mm to about 4.5 mm.

9. An article according to claim 8, wherein said thickness ranges from about 2 mm to about 4 mm.

10. An article according to claim 1, wherein the basis weight of said material of said fluid-receiving region ranges from about 25 g/m² to about 300 g/m².

11. An article according to claim 10, wherein said basis weight ranges from about 40 g/m² to about 200 g/m².

12. An article according to claim 11, wherein said basis weight ranges from about 50 m² to about 180 g/m².

13. An article according to claim 1, wherein each said fluid-receiving region is adapted to release to said fluid-storage region substantially all the fluid which said fluid-receiving region receives.

14. An article according to claim 13, wherein each said fluid-receiving region is adapted to release at least 95% of said fluid to said fluid-storage region which said fluid-receiving region receives.

15. An article according to claim 14, wherein each said fluid-receiving region is adapted to release to the fluid-storage region at least 99% of the fluid which it receives.

16. An article according to claim 1, wherein said material of each said fluid-receiving region has a wet collapse value of not more than 45%.

17. An article according to claim 16, wherein said wet collapse value is not more than 40%.

18. An article according to claim 1, wherein said material of each said fluid-receiving region has a wet resilience value of not more than 40%.

19. An article according to claim 18, wherein said wet resilience value is not more than 25%.

20. An article according to claim 19, wherein the said wet resilience value is not more than 25%.

21. An article according to claim 1, wherein said material of each said fluid-receiving region has a wetting time of not more than 5 seconds.

22. An article according to claim 21, wherein said wetting time is not more than 2 seconds.

23. An article according to claim 1, wherein said fibers of each said fluid-receiving region comprise a synthetic plastic material.

24. An article according to claim 23, wherein said material of said fluid-receiving region is substantially hydrophilic.

25. An article according to claim 24, wherein said material of each said fluid-receiving region comprises a wetting agent.

26. An article according to claim 25, wherein said material of each said fluid-receiving region comprises bicomponent fibers having a polypropylene portion, and a portion having a surface exposed to the exterior of said bicomponent fibers, said bicomponent fibers being formed of a polyethylene resin.

27. An article according to claim 26, wherein said fibers of said fluid-receiving region substantially comprise said bicomponent fibers.

28. An article according to claim 27, wherein 100% of said fibers of each said fluid-receiving region are said bicomponent fibers.

29. An article according to claim 1, wherein said material of each said fluid-receiving region is formed using fibers having a diameter not more than 40 μm.

30. An article according to claim 29, wherein said fiber diameters range from about 15 μm to 20 about μm.

31. An article according to claim 1, wherein said fluid-storage region comprises an absorbent hydrogel material.

32. An article according to claim 31, wherein said fluid-storage region further comprises a cellulose material.

33. An article according to claim 32, wherein said fluid-storage region comprises a laminate having outer layers of cellulose-containing material and an intermediate layer of absorbent hydrogel material.

34. An article according to claim 32, wherein said fluid-storage region comprises a laminate having two outer layers and a central layer of cellulose-containing material, and two layers of absorbent hydrogel material positioned between said central layer and said two outer layers.

35. An article according to claim 31, wherein said absorbent hydrogel material comprises particulates.

36. An article according to claim 1, wherein said fluid-receiving region and said fluid storage region each form a sheet, each said sheet being positioned in face-to-face relationship with said other sheet.

37. An article according to claim 36, wherein said fluid-receiving sheet and said fluid-storage sheet are secured to one another by an adhesive.

38. An article according to claim 37, further comprising a fluid-permeable topsheet in face-to-face relationship with said first fluid-receiving sheet, on the opposite side thereof to the fluid-storage sheet, and a fluid-impermeable backsheet positioned to be in face-to-face relationship with said second fluid-receiving sheet.

39. An article according to claim 36, wherein at least one of said fluid-receiving regions comprises a plurality of sheet members.

40. An article according to claim 39, wherein at least one said fluid-receiving region comprises two sheet members.

41. An article according to claim 1, wherein said fluid-receiving regions comprise a dry laid web of staple fibers.

42. An article according to claim 1, wherein said material used for each said fluid-receiving region substantially comprises the same fibers.

43. An article according to claim 1, said article being shaped to form a pad suitable for incontinent females.

* * * * *